(12) United States Patent
Arnin

(10) Patent No.: US 11,129,726 B2
(45) Date of Patent: Sep. 28, 2021

(54) FACET DISTRACTION AND FUSION PROSTHESIS

(71) Applicant: Zygofix Ltd., Misgav (IL)

(72) Inventor: Uri Arnin, Kiryat Tivon (IL)

(73) Assignee: Zygofix Ltd., Misgav (IL)

( * ) Notice: Subject to any disclaimer, the term of this patent is extended or adjusted under 35 U.S.C. 154(b) by 0 days.

(21) Appl. No.: 15/759,573

(22) PCT Filed: Aug. 19, 2016

(86) PCT No.: PCT/IB2016/054971
§ 371 (c)(1),
(2) Date: Mar. 13, 2018

(87) PCT Pub. No.: WO2017/046667
PCT Pub. Date: Mar. 23, 2017

(65) Prior Publication Data
US 2019/0151109 A1    May 23, 2019

Related U.S. Application Data

(60) Provisional application No. 62/283,856, filed on Sep. 14, 2015, provisional application No. 62/285,437, filed on Oct. 29, 2015.

(51) Int. Cl.
*A61F 2/44* (2006.01)
*A61F 2/30* (2006.01)
*A61B 17/70* (2006.01)

(52) U.S. Cl.
CPC .......... *A61F 2/4405* (2013.01); *A61F 2/4455* (2013.01); *A61B 17/7064* (2013.01);
(Continued)

(58) Field of Classification Search
CPC .............. A61F 2/4405; A61F 2/30; A61F 2002/30108; A61F 2002/30316;
(Continued)

(56) References Cited

U.S. PATENT DOCUMENTS

2006/0241758 A1   10/2006  Peterman
2013/0116793 A1*  5/2013   Kloss ............... A61F 2/442
                                                 623/17.16

FOREIGN PATENT DOCUMENTS

EP       0621020       10/1994
WO    2005/037149       4/2005
(Continued)

OTHER PUBLICATIONS

PCT Search Report and Written Opinion PCT/IB2016/054971, dated Jan. 4, 2017.

*Primary Examiner* — Eduardo C Robert
*Assistant Examiner* — Christina Negrellirodriguez
(74) *Attorney, Agent, or Firm* — Dekel Patent Ltd.; David Klein

(57) ABSTRACT

A facet distraction prosthesis (10, 30) includes an array of facet distraction base elements (12, 32) connected to each other by one or more connector elements (14, 34). A pair of diagonally adjacent base elements (12, 32) are connected to each other by a set of or more connector elements (14, 34) which intersects with another set of one or more connector elements (14, 34) that connects another pair of diagonally adjacent base elements (12, 32). The connector elements (14, 34) are flexible so that the base elements (12, 32) can flex with respect to each other and adapt to a geometry of a facet joint.

14 Claims, 6 Drawing Sheets

(52) U.S. Cl.
CPC ............... *A61F 2002/30092* (2013.01); *A61F 2002/30235* (2013.01); *A61F 2002/30884* (2013.01); *A61F 2002/4415* (2013.01)

(58) Field of Classification Search
CPC ............ A61F 2002/30878; A61F 2/445; A61F 2002/4415; A61B 17/7062; A61B 17/7064
USPC .............................. 606/247; 623/17.11–17.16
See application file for complete search history.

(56) References Cited

FOREIGN PATENT DOCUMENTS

| | | |
|---|---|---|
| WO | 2009/006455 | 1/2009 |
| WO | 2010/030994 | 3/2010 |
| WO | 2012/116267 | 8/2012 |

\* cited by examiner

FACET DISTRACTION AND FUSION PROSTHESIS

FIELD OF THE INVENTION

The present invention relates generally to spinal implants and prostheses, and particularly to a facet distraction and fusion prosthesis designed to be placed between the two bony elements of a spinal facet joint.

BACKGROUND OF THE INVENTION

Spinal stenosis affects a significant portion of the population. Current surgical spinal fusion uses intervertebral pedicle screws and spinal cages, designed to be connected to two or more vertebrae.

However, the use of standard cages and pedicle screws system is quite invasive, which has known negative impacts. It would be advantageous to have a system that can obtain similar pain relief and clinical outcomes in a significantly less invasive manner.

Another problem is the significant variability of the geometry of the facet joints between different patients and different spinal levels of the same patient. It is difficult to adapt the spinal implant to the varying geometry.

SUMMARY OF THE INVENTION

The present invention seeks to provide an improved spinal prosthesis that can be placed between the two bony elements of a spinal facet joint and accommodate the significant variability of the geometry of the facet joints between different patients and different spinal levels of the same patient.

The clinical goal of this system is to increase the distance between the two bony elements and in this way perform indirect decompression of the spinal nerves. The system may also be firmly fixed to bones to enable long term fusion of the facet joint.

There is thus provided in accordance with an embodiment of the invention a facet distraction prosthesis including an array of facet distraction base elements, adjacent ones of the base elements being connected to each other by one or more connector elements, wherein a pair of diagonally adjacent ones of the base elements are connected to each other by a set of or more connector elements which intersects with another set of one or more connector elements that connects another pair of diagonally adjacent ones of the base elements, and wherein the connector elements are flexible so that adjacent ones of the base elements can flex with respect to each other and adapt to a geometry of a facet joint. One or more keels may extend from upper and/or lower faces of the base elements.

BRIEF DESCRIPTION OF THE DRAWINGS

The present invention will be understood and appreciated more fully from the following detailed description, taken in conjunction with the drawings in which.

DETAILED DESCRIPTION

Figure 1:
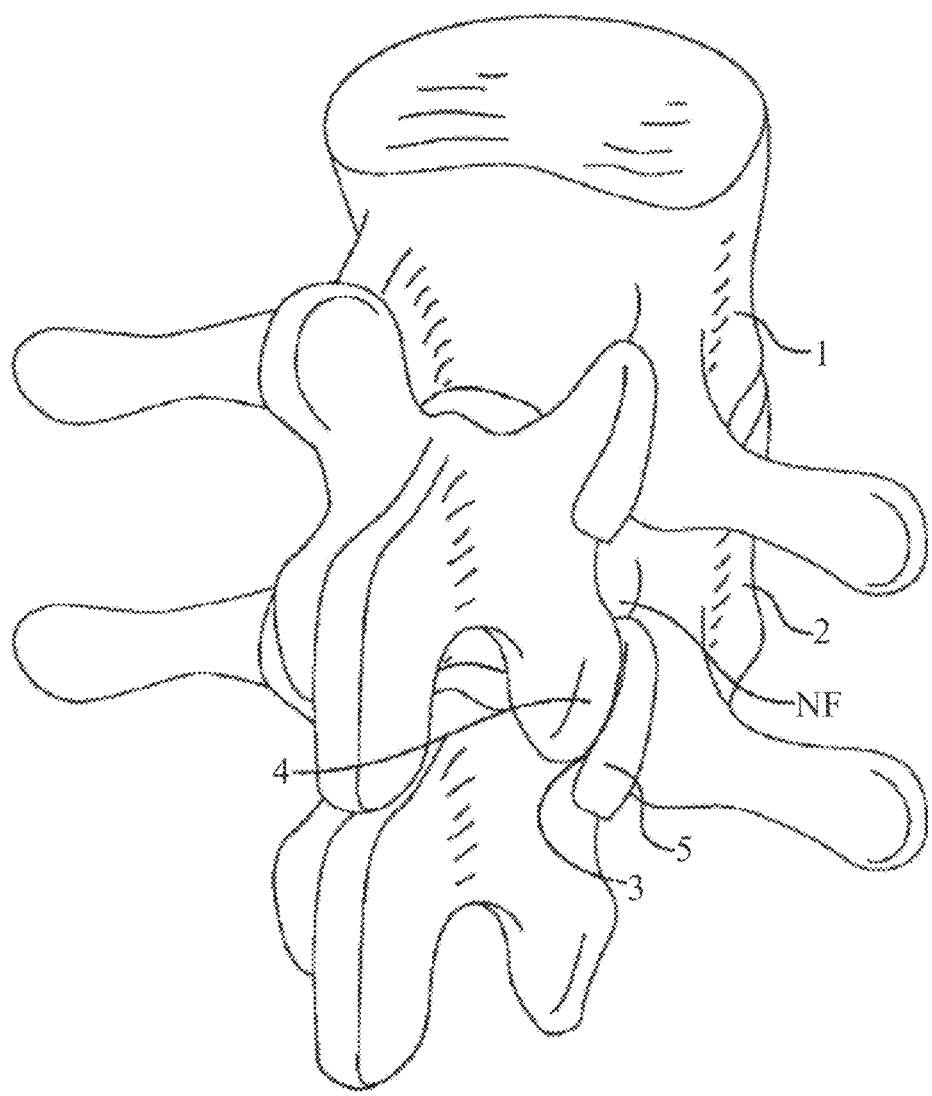
FIG. 1 is a simplified pictorial illustration of a portion of the spine with adjoining vertebrae prior to distraction.

In order to better understand the environment in which the facet distraction and fusion prosthesis is installed, reference is made to FIG. 1, which illustrates a portion of the spine with adjoining vertebrae prior to distraction. In this illustration, the neural foramen NF between a first vertebra 1 and a second vertebra 2 is stenotic. At the zygapophyseal joint capsule 3, there is no gap between the cephalic and caudal facets 4 and 5, respectively. Distraction is therefore recommended to create a gap between the facets and release the stenosis of the neural foramen.

Figure 2A:
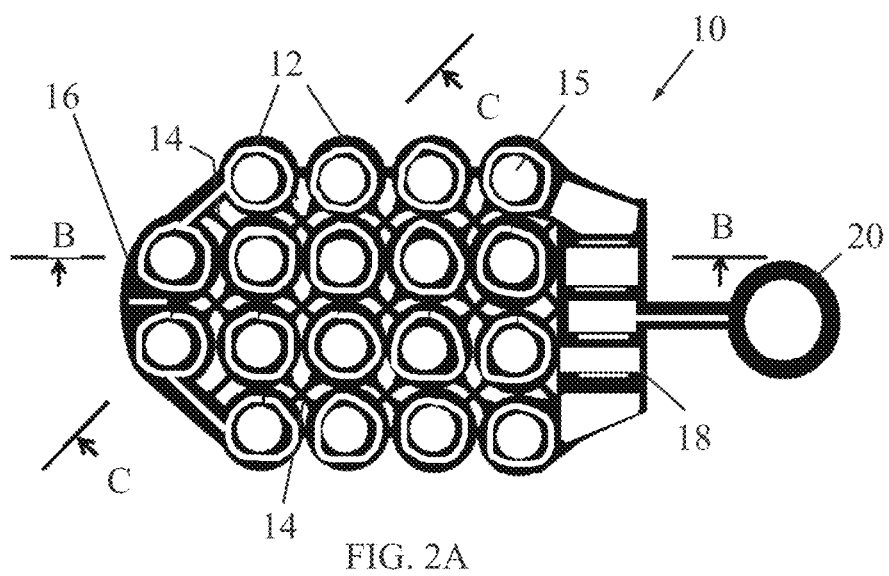
FIGS. 2A-2C are simplified pictorial and two different cutaway illustrations, respectively, of a facet distraction prosthesis, constructed and operative in accordance with a non-limiting embodiment of the present invention, with FIGS. 2B and 2C being taken along lines B-B and C-C, respectively, in FIG. 2A.
Figure 2B:
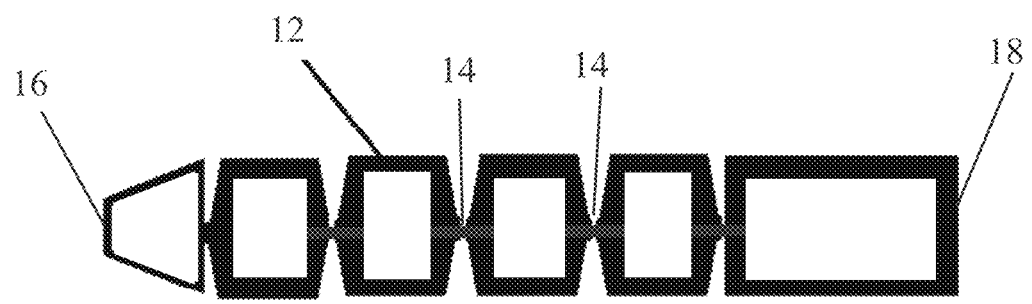
Figure 2C:
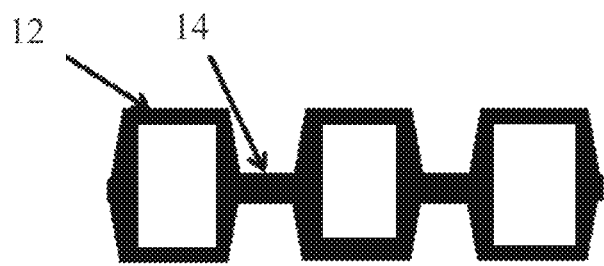

Reference is now made to FIGS. 2A-2C, which illustrate a facet distraction and fusion prosthesis 10, constructed and operative in accordance with a non-limiting embodiment of the present invention.

The facet distraction prosthesis 10 includes an array of facet distraction base elements 12, adjacent base elements 12 being connected to each other by one or more connector elements 14.

Base elements 12 may have any geometrical shape, such as but not limited to, circular, elliptic, round, square, rectangular, triangular, hexagonal, polygonal irregular, etc. One or more of the base elements 12 may have an aperture 15 formed therein. Aperture 15 may be a blind or through hole.

In the illustrated embodiment, a pair of diagonally adjacent base elements 12 are connected to each other by a set of or more connector elements 14 which intersects with another set of one or more connector elements 14 that connects another pair of diagonally adjacent base elements 12. The two crossed or intersecting sets of connector elements 14 may be perpendicular to each other or may be angled at other angles other than 90°. The base elements 12 at the periphery of the facet distraction prosthesis 10 may be connected to each other by one or more connector elements 14.

Connector elements 14 may have other shapes, such as rings, and do not necessarily intersect with each other.

Connector elements 14 may be made of the same material as base elements 12 or of a different material, such as but not limited to, a stainless steel alloy, titanium alloy, shape memory or superelastic material, plastic and others, or any combination thereof. Connector elements 14 may be flat, round or any other geometrical shape. Connector elements 14 are flexible so that adjacent base elements 12 can flex with respect to each other and adapt to the geometry of the facet joint.

The facet distraction prosthesis 10 may have a leading face 16 and a trailing face 18. The leading face 16 is the face that first enters the area of the facet joints when installing the prosthesis. The leading face 16 may have a tapered shape both as viewed from the top (FIG. 2A) and from the side (FIG. 2B), which facilitates insertion of the prosthesis. A grasping member 20 (e.g., a ring) may extend from the trailing face 18 for grasping the prosthesis for easy retrieval, adjustment or withdrawal.

As seen in FIGS. 2B and 2C, side walls of base elements 12 may be optionally chamfered, that is, slanted from upper and lower surfaces towards the middle of the base element 12. The chamfer helps the base elements 12 to move relative to each other so they can be self-arranged to fit the geometry of the facet joint.

Figure 3:
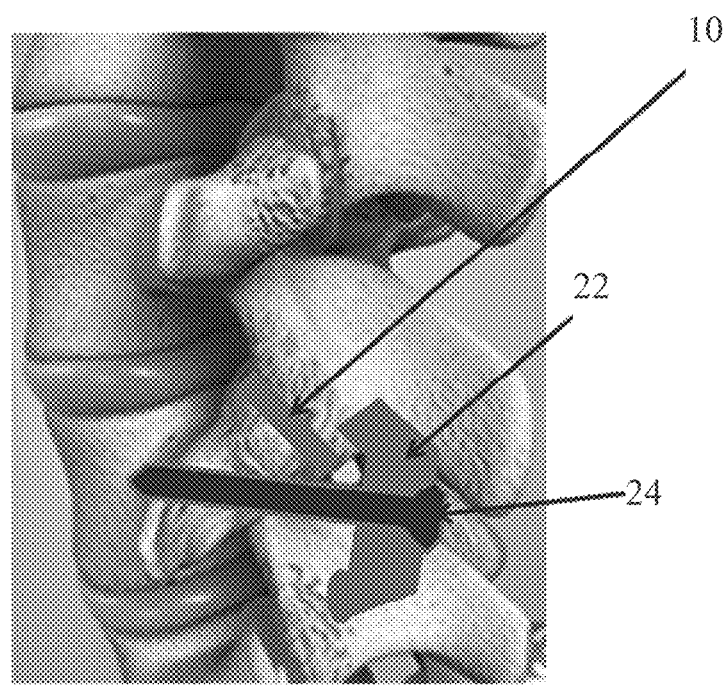
FIG. 3 is a simplified pictorial illustration of the facet distraction prosthesis installed in a facet joint.

Reference is now made to FIG. 3, which is a simplified pictorial illustration of the facet distraction prosthesis 10 after insertion between bony elements of the facet. A fixing element 22, such as but not limited to, a plate, bar, rod and the like of any suitable shape, may be used to lock the facet distraction prosthesis 10, and may be secured to bone with a bone screw 24.

Reference is now made to FIGS. 4A-4D, which illustrate a facet distraction prosthesis 30, constructed and operative in accordance with another non-limiting embodiment of the present invention.

Similarly to facet distraction prosthesis 10, facet distraction prosthesis 30 includes an array of facet distraction base elements 32, adjacent base elements 32 being connected to each other by one or more connector elements 34.

Base elements 32 may have any geometrical shape, as described above for FIG. 2A. One or more of the base elements 32 may have an aperture 35 formed therein. Aperture 35 may be a blind or through hole.

A pair of diagonally adjacent base elements 32 are connected to each other by a set of or more connector elements 34 which intersects with another set of one or more connector elements 34 that connects another pair of diagonally adjacent base elements 32. The two crossed or intersecting sets of connector elements 34 may be perpendicular to each other or may be angled at other angles other than 90°. The base elements 32 at the periphery of the facet distraction prosthesis 30 may be connected to each other by one or more connector elements 34. As noted above, connector elements in the shape of rings, having a round or irregular shape, for example, can also be used. Unlike facet distraction prosthesis 10, in facet distraction prosthesis 30, there may be a connector element 34 that is common to all base elements 32 along one or more of the sides of the periphery of facet distraction prosthesis 30.

As before, connector elements 34 are flexible so that adjacent base elements 32 can flex with respect to each other and adapt to the geometry of the facet joint.

The facet distraction prosthesis 30 may have a leading face 36 and a trailing face 38. The leading face 36 may have a tapered shape as viewed from the top and side. The facet distraction prosthesis 30 may include trailing tapered elements 40 that gradually increase in thickness in the direction of the trailing face 38, for grasping the prosthesis for easy retrieval, adjustment or withdrawal. The trailing face 38 may have an enlarged end of other stopping structure, not shown here, that can abut against the facet bone and limit the insertion depth.

As before, side walls of base elements 32 may be optionally chamfered.

Figure 4A:
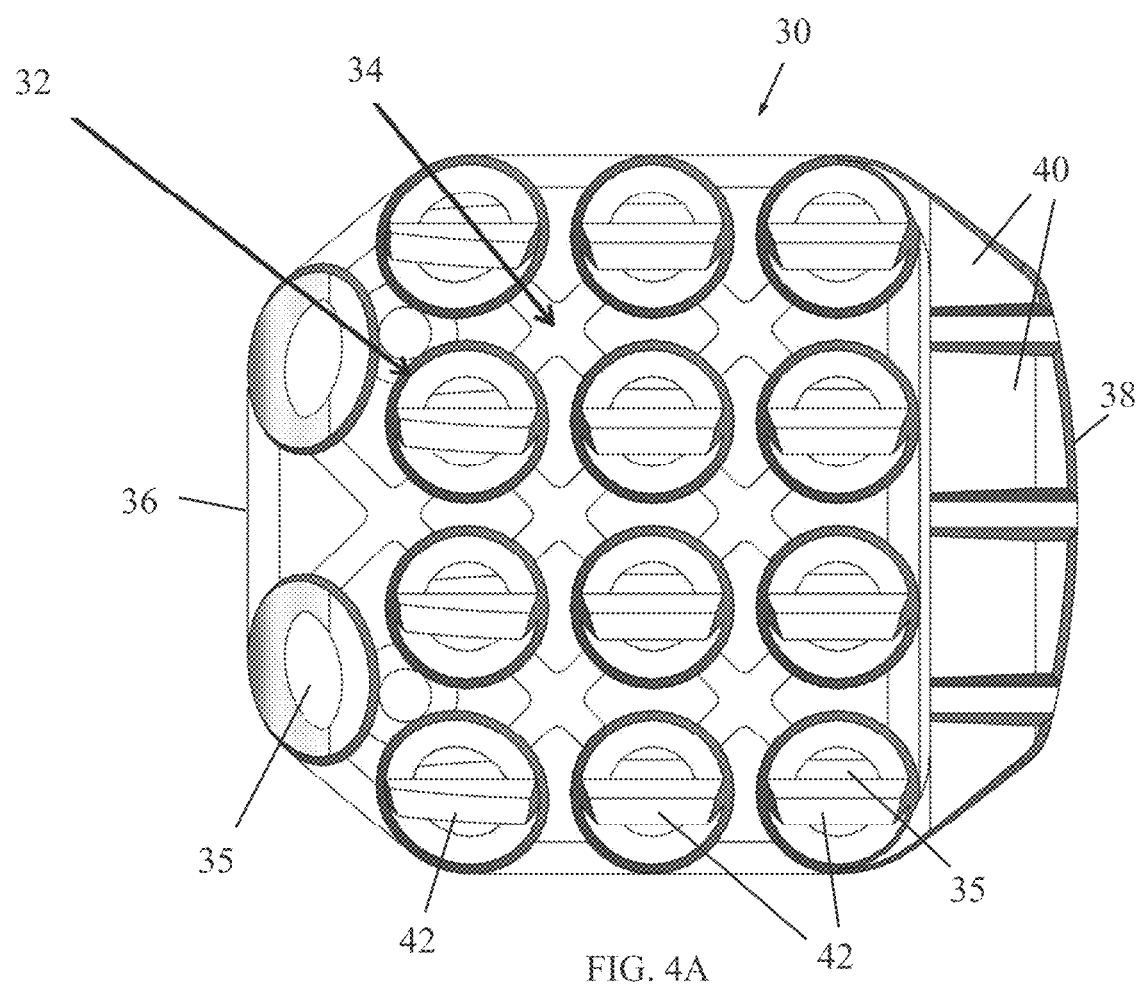
FIGS. 4A-4D are simplified top-view, perspective and two different side-view illustrations, respectively, of a facet distraction prosthesis with added keels, constructed and operative in accordance with another non-limiting embodiment of the present invention.
Figure 4B:
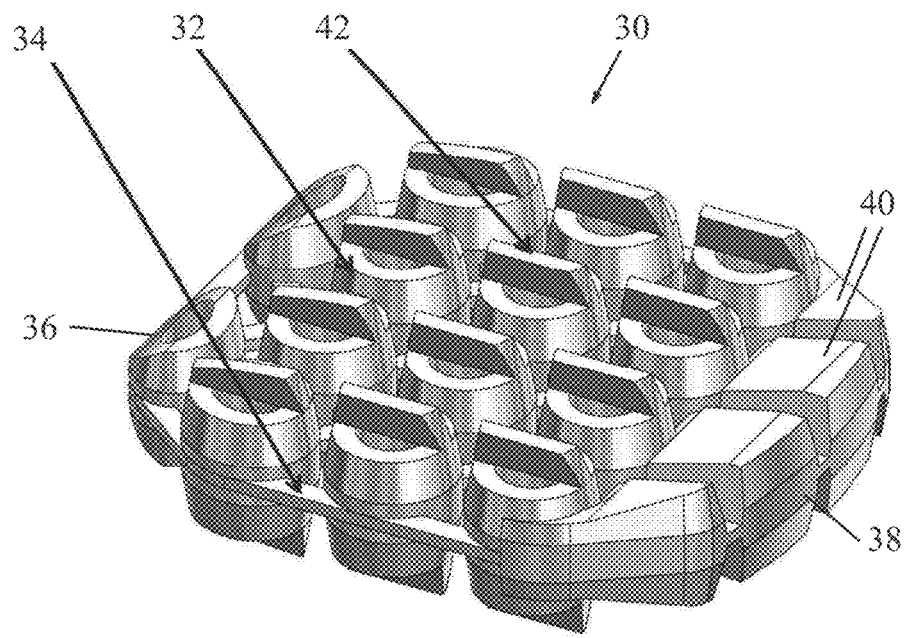
Figure 4C:
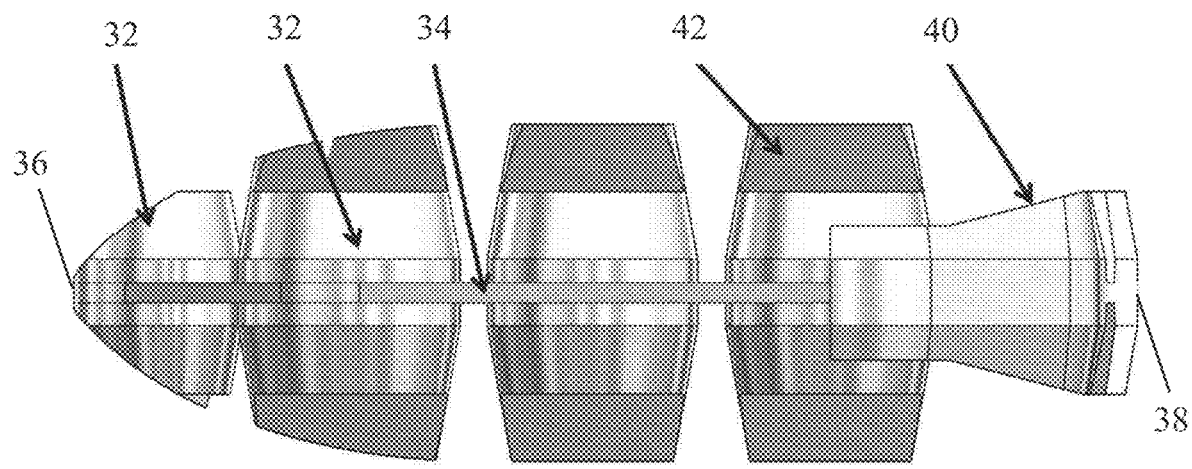
Figure 4D:
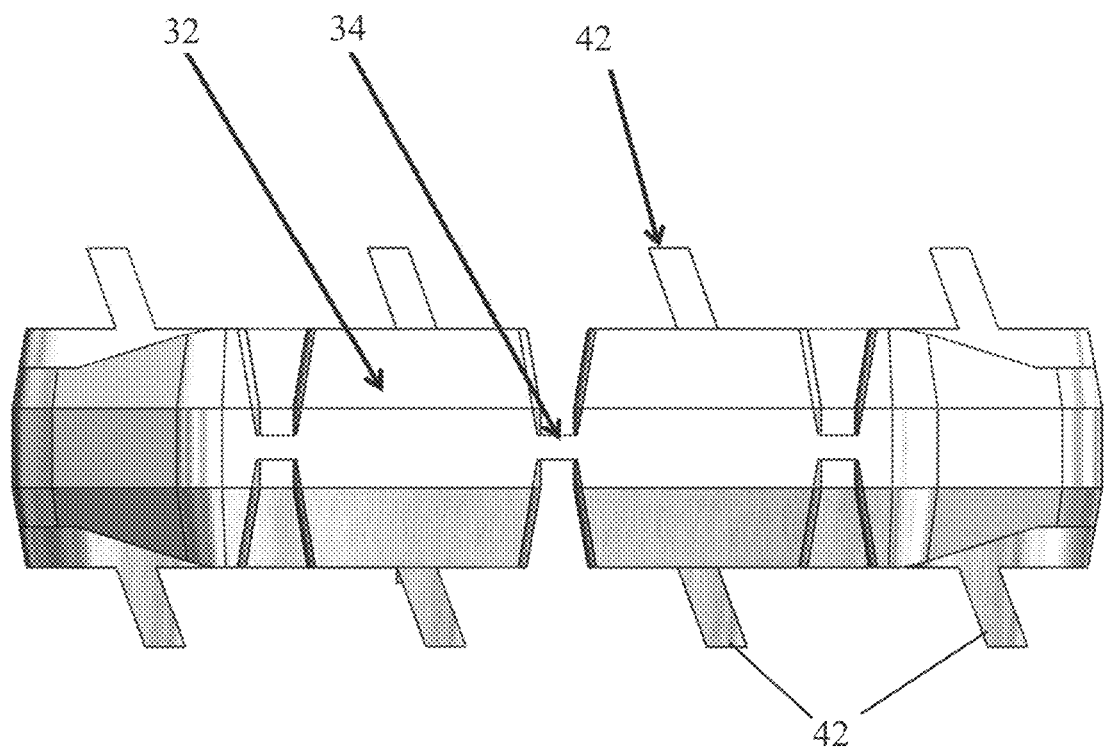

The facet distraction prosthesis 30 may include one or more keels 42 extending from upper and/or lower faces of base elements 32, which bite into spinal structure for increasing the holding force that holds the prosthesis in place in the spinal structure. As seen in FIG. 4A, keels 42 may be aligned to point towards the leading and trailing faces 36 and 38. The keels 42 near the leading face 36 may be chamfered towards the direction of leading face 36. As seen in FIG. 4D, keels 42 may be non-perpendicular with respect to the upper and lower surfaces of base elements 32.

The keels 42 may be shaped to be easily inserted but difficult to be pulled back, in order to prevent migration.

It is noted that any of the embodiments of the invention may be filled with bone graft to promote fusion of the bony elements to each other.

The invention claimed is:

1. A joint prosthesis comprising:
an array of joint distraction base elements, adjacent ones of said base elements being connected to each other by one or more connector elements;
wherein a pair of diagonally adjacent ones of said base elements are connected to each other by a set of one or more connector elements which non-parallelly intersects with another set of one or more connector elements that connects another pair of diagonally adjacent ones of said base elements, and wherein said connector elements are flexible so that adjacent ones of said base elements can flex with respect to each other and adapt to a geometry of a joint, wherein each of said one or more connector elements extends outwards from an outer contour of adjoining base elements, and wherein each of said one or more connector elements extends along a single longitudinal axis from a first end of the connector element that is joined to a first one of said base elements to a second end of the connector element, opposite to the first end, that is joined to a second one of said base elements.

2. The joint prosthesis according to claim 1, wherein one or more of said base elements have an aperture formed therein.

3. The joint prosthesis according to claim 1, wherein said intersecting sets of said connector elements are perpendicular to each other.

4. The joint prosthesis according to claim 1, wherein said joint prosthesis comprises a leading face and a trailing face.

5. The joint prosthesis according to claim 4, wherein said leading face has a tapered shape both as viewed from a top side thereof and a side face thereof.

6. The joint prosthesis according to claim 4, wherein a grasping member extends from said trailing face.

7. The joint prosthesis according to claim 4, further comprising trailing tapered elements that gradually increase in thickness in a direction of said trailing face.

8. The joint prosthesis according to claim 1, wherein side walls of said base elements are slanted from upper and lower surfaces towards a middle thereof.

9. The joint prosthesis according to claim 1, further comprising one or more keels extending from upper and/or lower faces of said base elements.

10. The joint prosthesis according to claim 9, wherein said one or more keels are aligned to point towards leading and trailing faces of said joint prosthesis.

11. The joint prosthesis according to claim 9, wherein some of said one or more keels are chamfered towards a direction of a leading face of said joint prosthesis.

12. The joint prosthesis according to claim 1, wherein said set of one or more connector elements crosses through or over said other set of one or more connector elements.

13. The joint prosthesis according to claim 1, wherein said base elements do not have straight sides.

14. The joint prosthesis according to claim 1, wherein said single longitudinal axis passes through a center of said base element to which said connector element is joined.

\* \* \* \* \*